(12) United States Patent
Gürtler et al.

(10) Patent No.: US 8,946,466 B2
(45) Date of Patent: Feb. 3, 2015

(54) METHOD FOR PRODUCING POLYETHER CARBONATE POLYOLS

(75) Inventors: Christoph Gürtler, Köln (DE); Jörg Hofmann, Krefeld (DE); Aurel Wolf, Wülfrath (DE); Stefan Grasser, Leverkusen (DE)

(73) Assignee: Bayer Intellectual Property GmbH, Monheim (DE)

( * ) Notice: Subject to any disclaimer, the term of this patent is extended or adjusted under 35 U.S.C. 154(b) by 40 days.

(21) Appl. No.: 13/698,694

(22) PCT Filed: May 13, 2011

(86) PCT No.: PCT/EP2011/057739
§ 371 (c)(1),
(2), (4) Date: Jan. 30, 2013

(87) PCT Pub. No.: WO2011/144523
PCT Pub. Date: Nov. 24, 2011

(65) Prior Publication Data
US 2013/0123532 A1 May 16, 2013

(30) Foreign Application Priority Data
May 18, 2010 (EP) .................................... 10163170

(51) Int. Cl.
*C07C 68/04* (2006.01)
*C08G 65/26* (2006.01)
*C08G 64/34* (2006.01)

(52) U.S. Cl.
CPC ............ *C07C 68/04* (2013.01); *C08G 65/2603* (2013.01); *C08G 65/2663* (2013.01); *C08G 64/34* (2013.01)
USPC ........................................................ 558/266

(58) Field of Classification Search
None
See application file for complete search history.

(56) References Cited

U.S. PATENT DOCUMENTS

| | | |
|---|---|---|
| 3,404,109 A | 10/1968 | Milgrom |
| 3,829,505 A | 8/1974 | Herold |
| 3,941,849 A | 3/1976 | Herold |
| 4,500,704 A | 2/1985 | Kruper, Jr. et al. |
| 5,158,922 A | 10/1992 | Hinney et al. |
| 5,470,813 A | 11/1995 | Le-Khac |
| 5,783,513 A | 7/1998 | Combs et al. |
| 6,716,788 B2 | 4/2004 | Eleveld et al. |
| 6,780,813 B1 | 8/2004 | Hofmann et al. |
| 7,008,900 B1 | 3/2006 | Hofmann et al. |
| 2003/0204042 A1 | 10/2003 | Moethrath et al. |
| 2005/0027145 A1 | 2/2005 | Hofmann et al. |
| 2006/0224010 A1* | 10/2006 | Hinz et al. ............. 558/276 |

FOREIGN PATENT DOCUMENTS

| | | |
|---|---|---|
| EP | 0700949 A2 | 3/1996 |
| EP | 0743093 A1 | 11/1996 |
| EP | 0761708 A2 | 3/1997 |
| EP | 1359177 A1 | 11/2003 |
| JP | 4145123 A | 5/1992 |
| WO | WO-97/40086 A1 | 10/1997 |
| WO | WO-98/16310 A1 | 4/1998 |
| WO | WO-00/47649 A1 | 8/2000 |
| WO | WO-01/39883 A1 | 6/2001 |
| WO | WO-01/80994 A1 | 11/2001 |
| WO | WO-03/106025 A1 | 12/2003 |
| WO | WO-2004/081082 A1 | 9/2004 |
| WO | WO-2006/103213 A1 | 10/2006 |
| WO | WO-2008/013731 A1 | 1/2008 |

OTHER PUBLICATIONS

Chen et al. React. Kinet. Catal. Lett, 2007, 91, 69-75.*
International Search Report for PCT/EP2011/057739 mailed Nov. 2, 2011.

* cited by examiner

*Primary Examiner* — Brandon Fetterolf
*Assistant Examiner* — Ana Z Muresan
(74) *Attorney, Agent, or Firm* — Drinker Biddle & Reath LLP

(57) ABSTRACT

The present invention relates to a process for the preparation of polyether carbonate polyols from one or more H-functional starter substances, one or more alkylene oxides and carbon dioxide in the presence of at least one double metal cyanide catalyst, wherein the cyanide-free metal salt, the metal cyanide salt or both the mentioned salts used for the preparation of the double metal cyanide catalyst contain(s) from 0.3 to 1.8 mol base equivalents (based on 1 mol of the metal cyanide salt used for the synthesis of the catalyst) of alkaline metal hydroxide, metal carbonate and/or metal oxide.

11 Claims, No Drawings

METHOD FOR PRODUCING POLYETHER CARBONATE POLYOLS

RELATED APPLICATIONS

This application is a national stage application (under 35 U.S.C. §371) of PCT/EP2011/057739, filed May 13, 2011, which claims benefit of European Application No. 10163170.3, filed May 18, 2010.

The present invention relates to a process for the preparation of polyether carbonate polyols from one or more H-functional starter substances, one or more alkylene oxides and carbon dioxide in the presence of at least one double metal cyanide catalyst, wherein the cyanide-free metal salt, the metal cyanide salt or both the mentioned salts used for the preparation of the double metal cyanide catalyst contain(s) from 0.3 to 1.8 mol base equivalents (based on 1 mol of the metal cyanide salt used for the synthesis of the catalyst) in the form of an alkaline metal hydroxide, metal carbonate and/or metal oxide.

The preparation of polyether carbonate polyols by catalytic reaction of alkylene oxides (epoxides) and carbon dioxide in the presence or absence of H-functional starter substances (starters) has been the subject of intensive research for more than 40 years (e.g. Inoue et al., Copolymerization of Carbon Dioxide and Epoxide with Organometallic Compounds; Die Makromolekulare Chemie 130, 210-220, 1969). This reaction, for example, using an H-functional starter compound is shown schematically in scheme (I), wherein R represents an organic radical such as alkyl, alkylaryl or aryl, each of which can also contain heteroatoms such as, for example, O, S, Si, etc., and wherein e and f represent an integer, and wherein the product shown here in scheme (I) for the polyether carbonate polyol is simply to be so understood that blocks having the structure shown can in principle be found again in the resulting polyether carbonate polyol but the sequence, number and length of the blocks as well as the OH functionality of the starter can vary and is not limited to the polyether carbonate polyol shown in scheme (I). This reaction (see scheme (I)) is ecologically very advantageous because this reaction represents the conversion of a greenhouse gas such as $CO_2$ into a polymer. The cyclic carbonate (for example for $R=CH_3$ propylene carbonate) shown in formula (I) is formed as a further product, actually a secondary product.

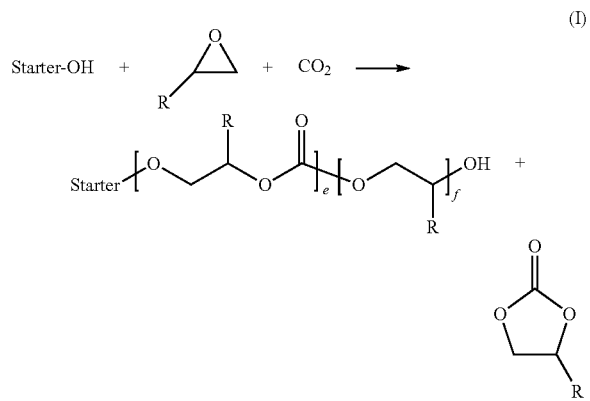

Activation within the scope of the invention denotes a step in which a partial amount of alkylene oxide compound, optionally in the presence of $CO_2$, is added to the DMC catalyst and then the addition of the alkylene oxide compound is interrupted, there being observed in the reactor the evolution of heat as a result of a subsequent exothermic chemical reaction, which can lead to a temperature peak ("hotspot"), and a pressure drop as a result of the reaction of alkylene oxide and optionally $CO_2$. The process step of activation is the period of time from the addition of the partial amount of alkylene oxide compound, optionally in the presence of $CO_2$, to the DMC catalyst to the occurrence of the evolution of heat. In general, the activation step can be preceded by a step for drying the DMC catalyst and optionally the starter at elevated temperature and/or reduced pressure, this step of drying not being part of the activation step within the scope of the present invention.

The formation of copolymers from epoxides (e.g. propylene oxide) and carbon dioxide has been known for a long time. For example, U.S. Pat. No. 4,500,704 describes the copolymerisation of carbon dioxide and propylene oxide using DMC catalysts. In that specification, for example, 71% of the propylene oxide had been converted after 48 hours in a reactor at 35° C. starting from a starter substance and 12.3 g of propylene oxide (212 mmol) and a carbon dioxide pressure of 48 bar. Of the 150.5 mmol of propylene oxide converted, 27 mmol (18%) reacted to form the generally undesirable secondary product propylene carbonate.

WO-A 2006/103213 discloses a process by means of which the formation of cyclic carbonates is reduced. This is achieved by adding to the DMC catalyst a $CO_2$-philic substance (e.g. perfluorinated compounds). Low propylene carbonate contents are found even at a high $CO_2$ pressure of 62 bar. Thus, for example, the content of propylene carbonate in Example 6 of the publication is only 2.7%, but the polydispersity of 7.98 is undesirably high.

Because propylene carbonate has an extraordinarily high boiling point of 240° C. at normal pressure, its separation from the reaction mixture is expensive and time-consuming. It is therefore desirable to develop a process for the copolymerisation of epoxides with carbon dioxide wherein the amounts of cyclic carbonate (such as, for example, propylene carbonate) formed are as small as possible. Accordingly, it was an object of the present invention to provide a process with which polyether carbonate polyols can be prepared with improved selectivity (i.e. as low a ratio as possible of cyclic carbonate to linear polyether carbonate), wherein the waiting time ("Time 1" in Table 1) until the temperature peak occurs in the copolymerisation is to be less than 120 minutes. A shorter waiting time has an advantageous effect on the economy of the process.

Surprisingly, it has now been found that the above-mentioned object is achieved by a process for the preparation of polyether carbonate polyols from one or more H-functional starter substances, one or more alkylene oxides and carbon dioxide in the presence of at least one DMC catalyst, wherein the cyanide-free metal salt, the metal cyanide salt or both the mentioned salts used for the preparation of the DMC catalyst contain(s) from 0.3 to 1.8 mol, preferably from 0.6 to 1.6 mol, particularly preferably from 0.8 to 1.4 mol base equivalents (based on 1 mol of the metal cyanide salt used for the synthesis of the catalyst) in the form of alkaline metal hydroxide, metal carbonate and/or metal oxide. Within the scope of the invention, base equivalents of an alkaline metal hydroxide, metal carbonate and/or metal oxide are understood as being the equivalents of the resulting hydroxide ions in a complete dissociation in water of the alkaline metal hydroxides, metal carbonates and/or metal oxides used. For example, 0.5 mol of a metal carbonate yields 1.0 mol base equivalents.

A preferred embodiment of the present invention is a process for the preparation of polyether carbonate polyols from one or more H-functional starter substances, one or more alkylene oxides and carbon dioxide in the presence of at least one DMC catalyst, characterised in that the DMC catalyst is prepared by reacting an aqueous solution of a cyanide-free metal salt with the aqueous solution of a metal cyanide salt in the presence of one or more organic complex ligands, for example in the presence of an ether or alcohol, wherein one or more alkaline metal hydroxides, metal carbonates and/or metal oxides are present either in the aqueous solution of the cyanide-free metal salt, in the aqueous solution of the metal cyanide salt or in both aqueous solutions, and wherein the sum of the alkaline metal hydroxides, metal carbonates and/or metal oxides used is from 0.3 to 1.8 mol, preferably from 0.6 to 1.6 mol, particularly preferably from 0.8 to 1.4 mol base equivalents (based on 1 mol of the metal cyanide salt used for the synthesis of the catalyst).

The process for the preparation of polyether carbonate polyols from at least one H-functional starter substance, at least one alkylene oxide and carbon dioxide in the presence of a DMC catalyst can be carried out continuously, semi-batchwise or discontinuously.

The polyether carbonate polyols obtained according to the invention generally have a functionality of at least 1, preferably from 2 to 8, particularly preferably from 2 to 6 and most particularly preferably from 2 to 4. The molecular weight is preferably from 400 to 10,000 g/mol and particularly preferably from 500 to 6000 g/mol.

In general, alkylene oxides having from 2 to 24 carbon atoms can be used for the process according to the invention. Alkylene oxides having from 2 to 24 carbon atoms are, for example, one or more compounds selected from the group consisting of ethylene oxide, propylene oxide, 1-butene oxide, 2,3-butene oxide, 2-methyl-1,2-propene oxide (isobutene oxide), 1-pentene oxide, 2,3-pentene oxide, 2-methyl-1,2-butene oxide, 3-methyl-1,2-butene oxide, 1-hexene oxide, 2,3-hexene oxide, 3,4-hexene oxide, 2-methyl-1,2-pentene oxide, 4-methyl-1,2-pentene oxide, 2-ethyl-1,2-butene oxide, 1-heptene oxide, 1-octene oxide, 1-nonene oxide, 1-decene oxide, 1-undecene oxide, 1-dodecene oxide, 4-methyl-1,2-pentene oxide, butadiene monoxide, isoprene monoxide, cyclopentene oxide, cyclohexene oxide, cycloheptene oxide, cyclooctene oxide, styrene oxide, methylstyrene oxide, pinene oxide, mono- or poly-epoxidised fats as mono-, di- and tri-glycerides, epoxidised fatty acids, $C_1$-$C_{24}$-esters of epoxidised fatty acids, epichlorohydrin, glycidol and derivatives of glycidol such as, for example, methyl glycidyl ether, ethyl glycidyl ether, 2-ethylhexyl glycidyl ether, allyl glycidyl ether, glycidyl methacrylate as well as epoxide-functional alkyloxysilanes such as, for example, 3-glycidyloxypropyltrimethoxysilane, 3-glycidyloxypropyltriethoxysilane, 3-glycidyloxypropyltripropoxysilane, 3-glycidyloxypropyl-methyl-dimethoxysilane, 3-glycidyloxypropyl-ethyldiethoxysilane, 3-glycidyloxypropyltriisopropoxysilane. Ethylene oxide and/or propylene oxide, in particular propylene oxide, are preferably used as the alkylene oxides.

There can be used as the suitable H-functional starter substance compounds having H atoms active for the alkoxylation. Groups which have active H atoms and which are active for the alkoxylation are, for example, —OH, —NH$_2$ (primary amines), —NH— (secondary amines), —SH and —CO$_2$H; —OH and —NH$_2$ are preferred; —OH is particularly preferred. There is used as the H-functional starter substance, for example, one or more compounds selected from mono- or poly-hydric alcohols, mono- or poly-valent amines, polyvalent thiols, carboxylic acids, aminoalcohols, aminocarboxylic acids, thioalcohols, hydroxy esters, polyether polyols, polyester polyols, polyester ether polyols, polyether carbonate polyols, polycarbonate polyols, polycarbonates, polyethyleneimines, polyether amines (e.g. so-called Jeffamine® from Huntsman, such as, for example, D-230, D-400, D-2000, T-403, T-3000, T-5000 or corresponding products from BASF, such as, for example, polyether amine D230, D400, D200, T403, T5000), polytetrahydrofurans (e.g. PolyTHF® from BASF, such as, for example, PolyTHF® 250, 650S, 1000, 1000S, 1400, 1800, 2000), polytetrahydrofuranamines (BASF product polytetrahydrofuranamine 1700), polyether thiols, polyacrylate polyols, castor oil, the mono- or di-glyceride of ricinoleic acid, monoglycerides of fatty acids, chemically modified mono-, di- and/or tri-glycerides of fatty acids, and $C_1$-$C_{24}$-alkyl fatty acid esters that contain on average at least 2 OH groups per molecule. The $C_1$-$C_{24}$-alkyl fatty acid esters that contain on average at least 2 OH groups per molecule are, for example, commercial products such as Lupranol Balance® (BASF AG), Merginol® types (Hobum Oleochemicals GmbH), Sovermol® types (Cognis Deutschland GmbH & Co. KG) and Soyol®™ types (USSC Co.).

There can be used as monofunctional starter substances alcohols, amines, thiols and carboxylic acids. There can be used as monofunctional alcohols: methanol, ethanol, 1-propanol, 2-propanol, 1-butanol, 2-butanol, tert-butanol, 3-buten-1-ol, 3-butyn-1-ol, 2-methyl-3-buten-2-ol, 2-methyl-3-butyn-2-ol, propargyl alcohol, 2-methyl-2-propanol, 1-tert-butoxy-2-propanol, 1-pentanol, 2-pentanol, 3-pentanol, 1-hexanol, 2-hexanol, 3-hexanol, 1-heptanol, 2-heptanol, 3-heptanol, 1-octanol, 2-octanol, 3-octanol, 4-octanol, phenol, 2-hydroxybiphenyl, 3-hydroxybiphenyl, 4-hydroxybiphenyl, 2-hydroxypyridine, 3-hydroxypyridine, 4-hydroxypyridine. There are suitable as monofunctional amines: butylamine, tert-butylamine, pentylamine, hexylamine, aniline, aziridine, pyrrolidine, piperidine, morpholine. There can be used as monofunctional thiols: ethanethiol, 1-propanethiol, 2-propanethiol, 1-butanethiol, 3-methyl-1-butanethiol, 2-butene-1-thiol, thiophenol. There may be mentioned as monofunctional carboxylic acids: formic acid, acetic acid, propionic acid, butyric acid, fatty acids such as stearic acid, palmitic acid, oleic acid, linoleic acid, linolenic acid, benzoic acid, acrylic acid.

Polyhydric alcohols suitable as H-functional starter substances are, for example, dihydric alcohols (such as, for example, ethylene glycol, diethylene glycol, propylene glycol, dipropylene glycol, 1,3-propanediol, 1,4-butanediol, 1,4-butenediol, 1,4-butynediol, neopentyl glycol, 1,5-pentanediol, methylpentanediols (such as, for example, 3-methyl-1,5-pentanediol), 1,6-hexanediol; 1,8-octanediol, 1,10-decanediol, 1,12-dodecanediol, bis-(hydroxymethyl)-cyclohexanes (such as, for example, 1,4-bis-(hydroxymethyl) cyclohexane), triethylene glycol, tetraethylene glycol, polyethylene glycols, dipropylene glycol, tripropylene glycol, polypropylene glycols, dibutylene glycol and polybutylene glycols); trihydric alcohols (such as, for example, trimethylolpropane, glycerol, trishydroxyethyl isocyanurate, castor oil); tetrahydric alcohols (such as, for example, pentaerythritol); polyalcohols (such as, for example, sorbitol, hexitol, sucrose, starch, starch hydrolysates, cellulose, cellulose hydrolysates, hydroxy-functionalised fats and oils, in particular castor oil), as well as all modification products of the above-mentioned alcohols with different amounts of ε-caprolactone.

The H-functional starter substances can also be selected from the substance class of the polyether polyols, in particular those having a molecular weight Mn in the range from 100 to 4000 g/mol. Preference is given to polyether polyols that are composed of repeating ethylene oxide and propylene oxide units, preferably having a content of from 35 to 100% propylene oxide units, particularly preferably having a content of from 50 to 100% propylene oxide units. These can be random copolymers, gradient copolymers, alternating or block copolymers of ethylene oxide and propylene oxide. Suitable polyether polyols composed of repeating propylene oxide and/or ethylene oxide units are, for example, the Desmophen®, Acclaim®, Arcol®, Baycoll®, Bayfill®, Bayflex®, Baygal®, PET® and polyether polyols from Bayer MaterialScience AG (such as, for example, Desmophen® 3600Z, Desmophen® 1900U, Acclaim® Polyol 2200, Acclaim® Polyol 40001, Arcol® Polyol 1004, Arcol® Polyol 1010, Arcol® Polyol 1030, Arcol® Polyol 1070, Baycoll® BD 1110, Bayfill® VPPU 0789, Baygal® K55, PET® 1004, Polyether® S180). Further suitable homo-polyethylene oxides are, for example, the Pluriol® E brands from BASF SE, suitable homo-polypropylene oxides are, for example, the Pluriol® P brands from BASF SE, suitable mixed copolymers of ethylene oxide and propylene oxide are, for example, the Pluronic® PE or Pluriol® RPE brands from BASF SE.

The H-functional starter substances can also be selected from the substance class of the polyester polyols, in particular those having a molecular weight Mn in the range from 200 to 4500 g/mol. At least difunctional polyesters are used as polyester polyols. Polyester polyols preferably consist of alternating acid and alcohol units. There are used as acid components, for example, succinic acid, maleic acid, maleic anhydride, adipic acid, phthalic anhydride, phthalic acid, isophthalic acid, terephthalic acid, tetrahydrophthalic acid, tetrahydrophthalic anhydride, hexahydrophthalic anhydride or mixtures of the mentioned acids and/or anhydrides. There are used as alcohol components, for example, ethanediol, 1,2-propanediol, 1,3-propanediol, 1,4-butanediol, 1,5-pentanediol, neopentyl glycol, 1,6-hexanediol, 1,4-bis-(hydroxymethyl)-cyclohexane, diethylene glycol, dipropylene glycol, trimethylolpropane, glycerol, pentaerythritol or mixtures of the mentioned alcohols. If divalent or polyvalent polyether polyols are used as the alcohol component, polyester ether polyols which can likewise be used as starter substances for the preparation of the polyether carbonate polyols are obtained. Preferably, polyether polyols with Mn=from 150 to 2000 g/mol are used for the preparation of the polyester ether polyols.

Polycarbonate diols can further be used as H-functional starter substances, in particular polycarbonate diols having a molecular weight Mn in the range from 150 to 4500 g/mol, preferably from 500 to 2500 g/mol, which are prepared, for example, by reaction of phosgene, dimethyl carbonate, diethyl carbonate or diphenyl carbonate and difunctional alcohols or polyester polyols or polyether polyols. Examples of polycarbonates are to be found, for example, in EP-A 1359177. For example, there can be used as polycarbonate diols the Desmophen® C types from Bayer MaterialScience AG, such as, for example, Desmophen® C 1100 or Desmophen® C 2200.

In a further embodiment of the invention, polyether carbonate polyols can be used as the H-functional starter substances. In particular, polyether carbonate polyols that are obtainable by the process according to the invention described herein are used. These polyether carbonate polyols used as H-functional starter substances are prepared beforehand in a separate reaction step.

The H-functional starter substances generally have a functionality (i.e. number of H atoms active for the polymerisation per molecule) of from 1 to 8, preferably 2 or 3. The H-functional starter substances are used either individually or in the form of a mixture of at least two H-functional starter substances.

Preferred H-functional starter substances are alcohols of the general formula (II)

$$HO-(CH_2)_x-OH \qquad (II)$$

wherein x is a number from 1 to 20, preferably an even number from 2 to 20. Examples of alcohols according to formula (II) are ethylene glycol, 1,4-butanediol, 1,6-hexanediol, 1,8-octanediol, 1,10-decanediol and 1,12-dodecanediol. Further preferred H-functional starter substances are neopentyl glycol, trimethylolpropane, glycerol, pentaerythritol, reaction products of the alcohols according to formula (II) with ε-caprolactone, for example reaction products of trimethylolpropane with ε-caprolactone, reaction products of glycerol with ε-caprolactone, as well as reaction products of pentaerythritol with ε-caprolactone. Further preferred as H-functional starter substances are diethylene glycol, dipropylene glycol, castor oil, sorbitol, and polyether polyols composed of repeating polyalkylene oxide units.

Particularly preferably, the H-functional starter substances are one or more compounds selected from the group consisting of ethylene glycol, propylene glycol, 1,3-propanediol, 1,3-butanediol, 1,4-butanediol, 1,5-pentanediol, 2-methyl-1,3-propanediol, neopentyl glycol, 1,6-hexanediol, 1,8-octanediol, diethylene glycol, dipropylene glycol, glycerol, trimethylolpropane, di- and tri-functional polyether polyols, the polyether polyol being composed of a di- or tri-H-functional starter substance and propylene oxide or of a di- or tri-H-functional starter substance, propylene oxide and ethylene oxide. The polyether polyols preferably have a molecular weight Mn in the range from 62 to 4500 g/mol and a functionality of from 2 to 3, and in particular a molecular weight Mn in the range from 62 to 3000 g/mol and a functionality of from 2 to 3.

The preparation of the polyether carbonate polyols is carried out by catalytic addition of carbon dioxide and alkylene oxides to H-functional starter substances. Within the scope of the invention, "H-functional" is understood as being the number of H atoms active for the alkoxylation per molecule of the starter substance.

DMC catalysts are known in principle from the prior art (see e.g. U.S. Pat. No. 3,404,109, U.S. Pat. No. 3,829,505, U.S. Pat. No. 3,941,849 and U.S. Pat. No. 5,158,922). DMC catalysts which are described, for example, in U.S. Pat. No. 5,470,813, EP-A 700 949, EP-A 743 093, EP-A 761 708, WO 97/40086, WO 98/16310 and WO 00/47649 have a very high activity in the homopolymerisation of epoxides and permit the preparation of polyether polyols at very low catalyst concentrations (25 ppm or less), so that separation of the catalyst from the finished product is generally no longer required. A typical example is the highly active DMC catalysts described in EP-A 700 949, which contain, in addition to a double metal cyanide compound (e.g. zinc hexacyanocobaltate(III)) and an organic complex ligand (e.g. tert-butanol), also a polyether having a number-average molecular weight greater than 500 g/mol.

The preparation of alkaline DMC catalysts has been disclosed in U.S. Pat. No. 5,783,513. The described invention provided DMC catalysts having an alkalinity in the range from 0.2 to about 2.0 wt. % as metal oxide based on the mass of metal salt used to prepare the catalyst. These substantially non-crystalline catalysts resulted in an improved viscosity and a lower degree of unsaturation in the preparation of polyether polyols from alkylene oxides. The catalysts were accordingly used only in the homopolymerisation of propylene oxide. The specification contains no reference to copolymerisation using carbon dioxide.

U.S. Pat. No. 6,716,788 B2 discloses the preparation of alkaline DMC catalysts in the presence of from 0.03 to 0.4 mol of an alkaline metal compound (addition of oxides and/or hydroxides), based on the amount of metal salt used, which is reacted with metal cyanide salt. The DMC catalysts so prepared are used in the homopolymerisation of epoxides in the absence of carbon dioxide. There is no reference to copolymerisation using carbon dioxide.

The DMC catalysts according to the invention are preferably obtained by (i) in the first step, reacting an aqueous solution of a cyanide-free metal salt with the aqueous solution of a metal cyanide salt in the presence of one or more organic complex ligands, for example in the presence of an ether or alcohol, wherein one or more alkaline metal hydroxides, metal carbonates and/or metal oxides are present either in the aqueous solution of the cyanide-free metal salt, in the aqueous solution of the metal cyanide salt or in both the aqueous solutions and wherein the sum of the alkaline metal hydroxides, metal carbonates and/or metal oxides used is from 0.3 to 1.8 mol, preferably from 0.6 to 1.6 mol, particularly preferably from 0.8 to 1.4 mol base equivalents (based on 1 mol of the metal cyanide salt used for the synthesis of the catalyst), (ii) wherein in the second step the solid is separated from the suspension obtained from (i) by known techniques (such as centrifugation or filtration), (iii) wherein optionally in a third step the isolated solid is washed with an aqueous solution of an organic complex ligand (e.g. by being resuspended and then isolated again by filtration or centrifugation), (iv) wherein the resulting solid, optionally after pulverisation, is then dried at temperatures of generally from 20 to 100° C. and at pressures of generally from 0.1 mbar to normal pressure (1013 mbar), and wherein in the first step or immediately after the precipitation of the double metal cyanide compound (second step), one or more organic complex ligands, preferably in excess (based on the double metal cyanide compound), and optionally further complex-forming components are added.

The double metal cyanide compounds contained in the DMC catalysts according to the invention are the reaction products of water-soluble cyanide-free metal salts and water-soluble metal cyanide salts, wherein the cyanide-free metal salt, the metal cyanide salt or both the mentioned salts used for the preparation of the DMC catalyst contain(s) from 0.3 to 1.8 mol, preferably from 0.6 to 1.6 mol, particularly preferably from 0.8 to 1.4 mol base equivalents (based on 1 mol of the metal cyanide salt used for the synthesis of the catalyst) in the form of an alkaline metal hydroxide, metal carbonate and/or metal oxide.

For example, an aqueous solution of zinc chloride (preferably in excess, based on the metal cyanide salt such as, for example, potassium hexacyanocobaltate) and potassium hexacyanocobaltate is mixed and then dimethoxyethane (glyme) or tert-butanol (preferably in excess, based on zinc hexacyanocobaltate) is added to the resulting suspension, wherein the potassium hexacyanocobaltate used has previously been mixed with from 0.3 to 1.8 mol, preferably from 0.6 to 1.6 mol, particularly preferably from 0.8 to 1.4 mol base equivalents (based on 1 mol of the metal cyanide salt used for the synthesis of the catalyst) of alkaline metal hydroxide, metal carbonate and/or metal oxide.

Cyanide-free metal salts suitable for the preparation of the double metal cyanide compounds preferably have the general formula (III)

$$M(X)_n \qquad (III)$$

wherein

M is selected from the metal cations $Zn^{2+}$, $Fe^{2+}$, $Ni^{2+}$, $Mn^{2+}$, $Co^{2+}$, $Sr^{2+}$, $Sn^{2+}$, $Pb^{2+}$ and $Cu^{2+}$, M is preferably $Zn^{2+}$, $Fe^{2+}$, $Co^{2+}$ or $Ni^{2+}$, X are one or more (i.e. different) anions, preferably an anion selected from the group of the halides (i.e. fluoride, chloride, bromide, iodide), hydroxide, sulfate, carbonate, cyanate, thiocyanate, isocyanate, isothiocyanate, carboxylate, oxalate and nitrate;

n is 1 when X=sulfate, carbonate or oxalate, and n is 2 when X=halide, hydroxide, cyanate, thiocyanate, isocyanate, isothiocyanate or nitrate, or suitable cyanide-free metal salts have the general formula (IV)

$$M_r(X)_3 \qquad (IV)$$

wherein

M is selected from the metal cations $Fe^{3+}$, $Al^{3+}$ and $Cr^{3+}$,

X are one or more (i.e. different) anions, preferably an anion selected from the group of the halides (i.e. fluoride, chloride, bromide, iodide), hydroxide, sulfate, carbonate, cyanate, thiocyanate, isocyanate, isothiocyanate, carboxylate, oxalate and nitrate;

r is 2 when X=sulfate, carbonate or oxalate, and r is 1 when X=halide, hydroxide, cyanate, thiocyanate, isocyanate, isothiocyanate, carboxylate or nitrate, or suitable cyanide-free metal salts have the general formula (V)

$$M(X)_s \qquad (V)$$

wherein

M is selected from the metal cations $Mo^{4+}$, $V^{4+}$ and $W^{4+}$,

X are one or more (i.e. different) anions, preferably an anion selected from the group of the halides (i.e. fluoride, chloride, bromide, iodide), hydroxide, sulfate, carbonate, cyanate, thiocyanate, isocyanate, isothiocyanate, carboxylate, oxalate and nitrate;

s is 2 when X=sulfate, carbonate or oxalate, and s is 4 when X=halide, hydroxide, cyanate, thiocyanate, isocyanate, isothiocyanate, carboxylate or nitrate, or suitable cyanide-free metal salts have the general formula (VI)

$$M(X)_t \qquad (VI)$$

wherein

M is selected from the metal cations $Mo^{6+}$ and $W^{6+}$,

X are one or more (i.e. different) anions, preferably an anion selected from the group of the halides (i.e. fluoride, chloride, bromide, iodide), hydroxide, sulfate, carbonate, cyanate, thiocyanate, isocyanate, isothiocyanate, carboxylate, oxalate and nitrate;

t is 3 when X=sulfate, carbonate or oxalate, and t is 6 when X=halide, hydroxide, cyanate, thiocyanate, isocyanate, isothiocyanate, carboxylate or nitrate.

Examples of suitable cyanide-free metal salts are zinc chloride, zinc bromide, zinc iodide, zinc acetate, zinc acetylacetonate, zinc benzoate, zinc nitrate, iron(II) sulfate, iron(II) bromide, iron(II) chloride, cobalt(II) chloride, cobalt(II) thiocyanate, nickel(II) chloride and nickel(II) nitrate. Mixtures of different metal salts can also be used.

Metal cyanide salts suitable for the preparation of the double metal cyanide compounds preferably have the general formula (VII)

$(Y)_a M'(CN)_b (A)_c$ (VII)

wherein

M' is selected from one or more metal cations from the group consisting of Fe(II), Fe(III), Co(II), Co(III), Cr(II), Cr(III), Mn(II), Mn(III), Ir(III), Ni(II), Rh(III), Ru(II), V(IV) and V(V), M' is preferably one or more metal cations from the group consisting of Co(II), Co(III), Fe(II), Fe(III), Cr(III), Ir(III) and Ni(II), Y is selected from one or more metal cations from the group consisting of alkali metal (i.e. $Li^+$, $Na^+$, $K^+$, $Rb^+$, $Cs^+$) and alkaline earth metal (i.e. $Be^{2+}$, $Ca^{2+}$, $Mg^{2+}$, $Sr^{2+}$, $Ba^{2+}$, A is selected from one or more anions from the group consisting of halides (i.e. fluoride, chloride, bromide, iodide), hydroxide, sulfate, carbonate, cyanate, thiocyanate, isocyanate, isothiocyanate, carboxylate, oxalate or nitrate, and a, b and c are integers, the values for a, b and c being so chosen that the electroneutrality of the metal cyanide salt is given; a is preferably 1, 2, 3 or 4; b is preferably 4, 5 or 6; c preferably has the value 0.

Examples of suitable metal cyanide salts are potassium hexacyanocobaltate(III), potassium hexacyanoferrate(II), potassium hexacyanoferrate(III), calcium hexacyanocobaltate(III) and lithium hexacyanocobaltate(III).

Preferred double metal cyanide compounds which are contained in the DMC catalysts according to the invention are compounds of the general formula (VIII)

$M_x[M'_{x'}(CN)_y]_z$ (VIII), wherein M is as defined in formulae (III) to (VI) and
M' is as defined in formula (VII), and
x, x', y and z are integers and are so chosen that the electroneutrality of the double metal cyanide compound is given.
Preferably,
x=3, x'=1, y=6 and z=2,
M=Zn(II), Fe(II), Co(II) or Ni(II) and
M'=Co(III), Fe(III), Cr(III) or Ir(III).

Examples of suitable double metal halide compounds a) are zinc hexacyanocobaltate(III), zinc hexacyanoiridate(III), zinc hexacyanoferrate(III) and cobalt(II) hexacyanocobaltate (III). Further examples of suitable double metal cyanide compounds are to be found, for example, in U.S. Pat. No. 5,158, 922 (column 8, lines 29-66). Zinc hexacyanocobaltate(III) is particularly preferably used.

The alkaline metal hydroxides, carbonates and oxides used for the preparation of the DMC catalysts according to the invention are preferably the oxides or hydroxides of metals of groups 1a and 2a of the periodic system of the elements (see, for example, "Handbook of Chemistry and Physics, 63rd Edition"). Examples of suitable alkaline metal hydroxides, metal oxides and metal carbonates are sodium carbonate, sodium hydroxide, potassium carbonate, potassium hydroxide, calcium oxide, calcium hydroxide, barium hydroxide or barium oxide.

The organic complex ligands added in the preparation of the DMC catalysts are disclosed, for example, in U.S. Pat. No. 5,158,922 (see in particular column 6, lines 9 to 65), U.S. Pat. No. 3,404,109, U.S. Pat. No. 3,829,505, U.S. Pat. No. 3,941, 849, EP-A 700 949, EP-A 761 708, JP 4 145 123, U.S. Pat. No. 5,470,813, EP-A 743 093 and WO-A 97/40086. For example, there are used as organic complex ligands water-soluble, organic compounds with heteroatoms, such as oxygen, nitrogen, phosphorus or sulfur, which are able to form complexes with the double metal cyanide compound. Preferred organic complex ligands are alcohols, aldehydes, ketones, ethers, esters, amides, ureas, nitriles, sulfides and mixtures thereof. Particularly preferred organic complex ligands are aliphatic ethers (such as dimethoxyethane), water-soluble aliphatic alcohols (such as ethanol, isopropanol, n-butanol, isobutanol, sec-butanol, tert-butanol, 2-methyl-3-buten-2-ol and 2-methyl-3-butyn-2-ol), compounds which contain both aliphatic or cycloaliphatic ether groups and aliphatic hydroxyl groups (such as, for example, ethylene glycol mono-tert-butyl ether, diethylene glycol mono-tert-butyl ether, tripropylene glycol monomethyl ether and 3-methyl-3-oxetan-methanol). Most preferred organic complex ligands are selected from one or more compounds from the group consisting of dimethoxyethane, tert-butanol, 2-methyl-3-buten-2-ol, 2-methyl-3-butyn-2-ol, ethylene glycol mono-tert-butyl ether and 3-methyl-3-oxetan-methanol.

In the preparation of the DMC catalysts according to the invention there are optionally used one or more complex-forming component(s) from the compound classes of the polyethers, polyesters, polycarbonates, polyalkylene glycol sorbitan esters, polyalkylene glycol glycidyl ethers, polyacrylamide, poly(acrylamide-co-acrylic acid), polyacrylic acid, poly(acrylic acid-co-maleic acid), polyacrylonitrile, polyalkyl acrylates, polyalkyl methacrylates, polyvinyl methyl ether, polyvinyl ethyl ether, polyvinyl acetate, polyvinyl alcohol, poly-N-vinylpyrrolidone, poly(N-vinylpyrrolidone-co-acrylic acid), polyvinyl methyl ketone, poly(4-vinylphenol), poly(acrylic acid-co-styrene), oxazoline polymers, polyalkyleneimines, maleic acid and maleic anhydride copolymers, hydroxyethylcellulose and polyacetals, or of the glycidyl ethers, glycosides, carboxylic acid esters of polyhydric alcohols, gallic acids or salts, esters or amides thereof, cyclodextrins, phosphorus compounds, α,β-unsaturated carboxylic acid esters or ionic surface-active compounds.

In the preparation of the DMC catalysts according to the invention there are preferably reacted in the first step the aqueous solutions of the metal salt (e.g. zinc chloride), used in stoichiometric excess (at least 50 mol %) based on metal cyanide salt, that is to say at least a molar ratio of cyanide-free metal salt to metal cyanide salt of from 2.25 to 1.00, and of the metal cyanide salt (e.g. potassium hexacyanocobaltate) in the presence of the organic complex ligand (e.g. tert-butanol), wherein one or more alkaline metal hydroxides, metal carbonates and/or metal oxides are present either in the aqueous solution of the cyanide-free metal salt, in the aqueous solution of the metal cyanide salt or in both the aqueous solutions, so that a suspension forms which contains the double metal cyanide compound (e.g. zinc hexacyanocobaltate), water, excess cyanide-free metal salt, and the organic complex ligand.

The organic complex ligand can be present in the aqueous solution of the cyanide-free metal salt and/or of the metal cyanide salt, or it is added directly to the suspension obtained after precipitation of the double metal cyanide compound. It has been found to be advantageous to mix the aqueous solutions of the cyanide-free metal salt and of the metal cyanide salt, wherein one or more alkaline metal hydroxides, metal carbonates and/or metal oxides are present either in the aqueous solution of the cyanide-free metal salt, in the aqueous solution of the metal cyanide salt or in both the aqueous solutions, and the organic complex ligand with vigorous stirring. Optionally, the suspension formed in the first step is then treated with a further complex-forming component. The complex-forming component is preferably used in a mixture with water and organic complex ligand. A preferred process for carrying out the first step (i.e. the preparation of the suspension) takes place using a mixing nozzle, particularly preferably using a jet disperser as described in WO-A 01/39883.

In the second step, the solid (i.e. the precursor of the catalyst according to the invention) is isolated from the suspension by known techniques, such as centrifugation or filtration.

In a preferred variant, the isolated solid is then washed in a third process step with an aqueous solution of the organic complex ligand (e.g. by being resuspended and then isolated again by filtration or centrifugation). In this manner, water-soluble secondary products, for example, such as potassium chloride, can be removed from the catalyst according to the invention. Preferably, the amount of organic complex ligand in the aqueous wash solution is from 40 to 80 wt. %, based on the total solution.

Optionally, further complex-forming component, preferably in the range from 0.5 to 5 wt. %, based on the total solution, is added to the aqueous wash solution in the third step.

It is additionally advantageous to wash the isolated solid more than once. Preferably, the solid is washed in a first washing step (iii-1) with an aqueous solution of the unsaturated alcohol (e.g. by being resuspended and then isolated again by filtration or centrifugation) in order thus to remove, for example, water-soluble secondary products, such as potassium chloride, from the catalyst according to the invention. Particularly preferably, the amount of unsaturated alcohol in the aqueous wash solution is from 40 to 80 wt. %, based on the total solution of the first washing step. In the further washing steps (iii-2), either the first washing step is repeated once or several times, preferably from one to three times, or, preferably, a non-aqueous solution, such as, for example, a mixture or solution of organic complex ligand and further complex-forming component (preferably in the range from 0.5 to 5 wt. %, based on the total amount of the wash solution of step (iii-2)), is used as the wash solution and the solid is washed therewith once or several times, preferably from one to three times.

The isolated and optionally washed solid is then, optionally after pulverisation, dried at temperatures of generally from 20 to 100° C. and at pressures of generally from 0.1 mbar to normal pressure (1013 mbar).

A preferred process for isolating the DMC catalysts according to the invention from the suspension by filtration, filter cake washing and drying is described in WO-A 01/80994.

The invention also provides a process for the preparation of polyether carbonate polyols from one or more H-functional starter substances, one or more alkylene oxides and carbon dioxide in the presence of at least one DMC catalyst, wherein the cyanide-free metal salt, metal cyanide salt or both the mentioned salts used for the preparation of the DMC catalyst contain(s) from 0.3 to 1.8 mol, preferably from 0.6 to 1.6 mol, particularly preferably from 0.8 to 1.4 mol base equivalents (based on 1 mol of the metal cyanide salt used for the synthesis of the catalyst) in the form of an alkaline metal hydroxide, metal carbonate and/or metal oxide, and wherein (α) the H-functional starter substance, or a mixture of at least two H-functional starter substances, is placed in a reaction vessel and optionally water and/or other readily volatile compounds are removed by elevated temperature and/or reduced pressure ("drying"), wherein the DMC catalyst is added to the H-functional starter substance, or the mixture of at least two H-functional starter substances, before or after the drying, (β) for activation (β1) in a first activation step, a first partial amount (based on the total amount of the amount of alkylene oxides used in the activation and copolymerisation) of one or more alkylene oxides is added to the mixture resulting from step (α), wherein this addition of the partial amount of alkylene oxide can optionally take place in the presence of $CO_2$ but preferably takes place in the absence of $CO_2$, and wherein a waiting period is then observed until the temperature peak ("hotspot") that occurs as a result of the subsequent exothermic chemical reaction, and/or a pressure drop in the reactor occurs, (β2) in a second activation step, after the temperature peak reached in the preceding activation step, a second partial amount (based on the total amount of the amount of alkylene oxides used in the activation and copolymerisation) of one or more alkylene oxides is added to the mixture resulting from the preceding activation step, wherein this addition of the partial amount of alkylene oxide can optionally take place in the presence of $CO_2$ but preferably takes place in the absence of $CO_2$, and wherein a waiting period is then observed until the temperature peak ("hotspot") that occurs as a result of the subsequent exothermic chemical reaction, and/or a pressure drop in the reactor occurs, (β3) optionally in a third activation step, or further activation steps, after the temperature peak reached in the preceding activation step, step (β2) is repeated from zero to five times, preferably from one to four times, particularly preferably exactly once, wherein this addition of the partial amount, or these additions of the partial amounts, of alkylene oxide take(s) place in the absence of $CO_2$, and wherein a waiting period is then observed until the temperature peak ("hotspot") that occurs as a result of the subsequent exothermic chemical reaction, and/or a pressure drop in the reactor occurs, (β4) optionally in a further activation step, or further activation steps, after the temperature peak reached in the preceding activation step, step (β3) is repeated from one to five times, preferably from one to four times, particularly preferably exactly once, wherein this addition of the partial amount, or these additions of the partial amounts, of alkylene oxide take(s) place in the presence of $CO_2$, and wherein a waiting time is then observed until the temperature peak ("hotspot") that occurs as a result of the subsequent exothermic chemical reaction, and/or a pressure drop in the reactor occurs, (γ) one or more alkylene oxides and carbon dioxide are metered continuously into the mixture resulting from step (β) ("copolymerisation"). The alkylene oxides used for the copolymerisation can be the same as or different from the alkylene oxides used in the activation.

In a preferred embodiment, the partial amount of one or more alkylene oxides used in the activation in steps β1 to β4 is in each case from 2.0 to 15.0 wt. %, preferably from 2.5 to 14.0 wt. %, particularly preferably from 3.0 to 13.0 wt. % (based on the total amount of the amount of alkylene oxides used in the activation and copolymerisation).

Step (α):

For the preparation of polyether carbonate polyols by catalytic addition of alkylene oxides (epoxides) and carbon dioxide to H-functional starter substances (starters) in the presence of the DMC catalysts according to the invention, the H-functional starter substance, or a mixture of at least two H-functional starter substances, is placed in a reaction vessel. Optionally in step (α)

(α1) the H-functional starter substance, or a mixture of at least two H-functional starter substances, is placed in a reaction vessel and (α2) the temperature of the starter substance or of the mixture is brought to from 50 to 200° C., preferably from 80 to 160° C., particularly preferably from 100 to 140° C., and/or the pressure in the reactor is reduced to less than 500 mbar, preferably from 5 mbar to 100 mbar. A stream of nitrogen can also be passed through the reactor.

The DMC catalyst can already be present in the H-functional starter substance, or in the mixture of at least two H-functional starter substances, but it is also possible to add the DMC catalyst, which is then dry, to the H-functional starter substance, or the mixture of H-functional starter substances, only after the drying. The DMC catalyst be added in solid form or in the form of a suspension in an H-functional starter substance. If the catalyst is added in the form of a suspension, it is preferably added to the H-functional starter substance(s) before the drying.

Step (β3):

The metered addition of one or more alkylene oxides and optionally of the carbon dioxide takes place after drying of a starter substance or of the mixture of a plurality of starter substances and after the addition of the DMC catalyst, which is added in the form of a solid or in the form of a suspension before or after drying of the starter substance. If the DMC catalyst is added after drying of the starter substance, the DMC catalyst should preferably be dried, for example in an analogous process to the drying of the starter substance. The metered addition of one or more alkylene oxides and of the carbon dioxide can in principle take place in different ways. The start of the metered addition can take place from the vacuum or at a previously chosen preliminary pressure. The preliminary pressure is preferably established by passing in an inert gas such as, for example, nitrogen, the pressure (absolute) being set at from 10 mbar to 10 bar, preferably from 100 mbar to 8 bar and more preferably from 500 mbar to 6 bar. In a particularly preferred embodiment, the mixture of one or more starter substances and the DMC catalyst resulting from step (α) is subjected at a temperature of from 100° C. to 130° C. at least once, preferably three times, to an inert gas pressure (nitrogen or a noble gas such as, for example, argon) of from 1.5 bar to 10 bar (absolute), particularly preferably from 3 bar to 6 bar (absolute), and immediately thereafter, within a period of up to 15 minutes, the excess pressure is in each case reduced to 1 bar (absolute). Alternatively, in an embodiment which is likewise particularly preferred, inert gas (nitrogen or a noble gas such as, for example, argon) is passed at a temperature of from 40° C. to 150° C. into the mixture of one or more starter compounds and the DMC catalyst resulting from step (α) and at the same time a reduced pressure (absolute) of from 10 mbar to 800 mbar, particularly preferably from 50 mbar to 200 mbar, is applied.

Step (γ):

The metered addition of one or more alkylene oxides and of the carbon dioxide can take place simultaneously or sequentially, it being possible for the entire amount of carbon dioxide to be added at once or in a metered manner over the reaction time. A metered addition of the carbon dioxide is preferably carried out. The metered addition of one or more alkylene oxides takes place simultaneously or sequentially with the metered addition of the carbon dioxide. If a plurality of alkylene oxides are used in the synthesis of the polyether carbonate polyols, then the metered addition thereof can take place simultaneously or sequentially via separate metered additions or via one or more metered additions, at least two alkylene oxides being metered in as a mixture. Via the nature of the metered addition of the alkylene oxides and of the carbon dioxide it is possible to synthesise random, alternating, block-like or gradient-like polyether carbonate polyols.

The concentration of free alkylene oxides during the reaction in the reaction mixture is preferably from >0 to 40 wt. %, particularly preferably from >0 to 25 wt. %, most preferably from >0 to 15 wt. % (in each case based on the weight of the reaction mixture).

Preferably, an excess of carbon dioxide, based on the calculated amount of incorporated carbon dioxide in the polyether carbonate polyol, is used because an excess of carbon dioxide is advantageous due to the slowness of carbon dioxide to react. The amount of carbon dioxide can be established via the total pressure under the reaction conditions in question. The range from 0.01 to 120 bar, preferably from 0.1 to 110 bar, particularly preferably from 1 to 100 bar, has been found to be advantageous as the total pressure (absolute) for the copolymerisation for the preparation of the polyether carbonate polyols. For the process according to the invention it has further been shown that the copolymerisation for the preparation of the polyether carbonate polyols is advantageously carried out at from 50 to 150° C., preferably at from 60 to 145° C., particularly preferably at from 70 to 140° C. and most particularly preferably at from 110 to 120° C. If temperatures below 50° C. are set, the reaction comes to a halt. At temperatures above 150° C., the amount of undesirable secondary products increases considerably. It is further to be ensured that the $CO_2$ as far as possible changes from the gaseous state to the liquid and/or supercritical liquid state under the chosen reaction conditions. $CO_2$ can, however, also be added to the reactor in the form of a solid and then change into the liquid and/or supercritical liquid state under the chosen reaction conditions.

Particularly preferred reactors are: tubular reactor, stirrer vessel, loop reactor. Polyether polycarbonate polyols can be prepared in a stirrer vessel, the stirrer vessel being cooled, according to the design and mode of operation, via the reactor jacket, internal cooling surfaces and/or cooling surfaces located in a pump circuit. For safety reasons, the content of free epoxide should not exceed 15 wt. % in the reaction mixture of the stirrer vessel (see, for example, WO-A 2004/081082; page 3; line 14). Attention is therefore to be paid particularly to the metering rate of the epoxide both in semi-batch operation, where the product is not removed until the end of the reaction, and in continuous operation, where the product is removed continuously. The metering rate of the epoxide is to be so adjusted that the epoxide reacts completely sufficiently quickly despite the inhibiting effect of the carbon dioxide. It is possible to supply the carbon dioxide continuously or discontinuously. This depends on whether the epoxide is consumed quickly enough and whether the product is optionally to contain $CO_2$-free polyether blocks. The amount of carbon dioxide (indicated as pressure) can likewise vary during the addition of the epoxide. It is possible gradually to increase the $CO_2$ pressure during the addition of the epoxide or to lower it or leave it the same.

A further possible embodiment in the stirrer vessel for the copolymerisation (step γ) is characterised in that one or more H-functional starter compounds are metered into the reactor continuously during the reaction. The amount of H-functional starter compounds metered into the reactor continuously during the reaction is preferably at least 20 mol % equivalents, particularly preferably from 70 to 95 mol % equivalents (in each case based on the total amount of H-functional starter compounds).

The activated catalyst/starter mixture can be (further) copolymerised with epoxide and carbon dioxide in the stirrer vessel or in a different reaction vessel (tubular reactor or loop reactor).

In the case of a tubular reactor, the activated catalyst and the starter as well as the epoxide and carbon dioxide are pumped continuously through a tube. The molar ratios of the reactants vary according to the polymer that is desired. In a preferred embodiment, carbon dioxide is metered in in its supercritical form, that is to say virtually liquid form, in order to permit better miscibility of the components. There are advantageously fitted mixing elements for better mixing of the reactants, as are marketed, for example, by Ehrfeld Mikrotechnik BTS GmbH, or mixer/heat exchanger elements, which improve mixing and heat dissipation at the same time.

Even loop reactors can be used for the preparation of polyether polycarbonate polyols. In general, these include reactors with material recycling, such as, for example, a jet loop reactor, which can also be operated continuously, or a loop of tubular reactors. The use of a loop reactor is particularly advantageous because backmixing can be carried out here, so that the epoxide concentration should be low. In order to achieve complete conversion, a tube ("dwell tube") is frequently provided downstream.

The polyether carbonate polyols obtainable by the process according to the invention have a low content of secondary products and can be processed without difficulty, in particular by reaction with di- and/or poly-isocyanates to polyurethanes, in particular flexible polyurethane foams. For polyurethane applications, polyether carbonate polyols based on an H-functional starter compound having a functionality of at least 2 are preferably used. The polyether carbonate polyols obtainable by the process according to the invention can further be used in applications such as washing and cleaning agent formulations, drilling fluids, fuel additives, ionic and non-ionic surfactants, lubricants, process chemicals for paper or textile production, or cosmetic formulations. It is known to the person skilled in the art that, depending on the field of application in question, the polyether carbonate polyols to be used must satisfy particular material properties such as, for example, molecular weight, viscosity, polydispersity, functionality and/or hydroxyl number.

EXAMPLES

The weight- and number-average molecular weight of the resulting polymers was determined by means of gel permeation chromatography (GPC). The procedure according to DIN 55672-1: "Gel permeation chromatography, Part 1—Tetrahydrofuran as elution solvent" was followed. Polystyrene samples of known molar mass were used for calibration.

The OH number (hydroxyl number) was determined on the basis of DIN 53240-2, but pyridine was used as solvent instead of THF/dichloromethane. Titration was carried out with 0.5 molar ethanolic KOH (end point recognition by means of potentiometry). Castor oil with certified OH number was used as test substance. The indication of the unit in "mg/g" refers to mg [KOH]/g [polyether carbonate polyol].

The amount of incorporated $CO_2$ in the resulting polyether carbonate polyol, and the ratio of propylene carbonate to polyether carbonate polyol, were determined by means of $^1$H-NMR (Bruker, DPX 400, 400 MHz; pulse program zg30, waiting time d1: 10 s, 64 scans). The sample was dissolved in each case in deuterated chloroform. The relevant resonances in the $^1$H-NMR (based on TMS=0 ppm) are as follows:
cyclic carbonate (which was formed as secondary product)
resonance at 4.5 ppm, carbonate, resulting from carbon dioxide incorporated in the polyether carbonate polyol (resonances at 5.1 to 4.8 ppm), unreacted PO with resonance at 2.4 ppm, polyether polyol (i.e. without incorporated carbon dioxide) with resonances at 1.2 to 1.0 ppm, the 1,8-octanediol incorporated as starter molecule with a resonance at 1.6 to 1.52 ppm.

The molar amount of carbonate incorporated in the polymer in the reaction mixture is calculated according to formula (IX) as follows, wherein the following abbreviations are used:
F(4.5)=resonance area at 4.5 ppm for cyclic carbonate (corresponds to an H atom)
F(5.1-4.8)=resonance area at 5.1-4.8 ppm for polyether carbonate polyol and an H atom for cyclic carbonate
F(2.4)=resonance area at 2.4 ppm for free, unreacted PO
F(1.2-1.0)=resonance area at 1.2-1.0 ppm for polyether polyol
F(1.6-1.52)=resonance area at 1.6 to 1.52 ppm for 1,8-octanediol (starter)

Taking into account the relative intensities, the polymer-bonded carbonate ("linear carbonate" LC) in the reaction mixture was converted to mol % according to the following formula (IX):

$$LC = \frac{F(5.1-4.8) - F(4.5)}{F(5.1-4.8) + F(2.4) + 0.33 * F(1.2-1.0) + 0.25 * F(1.6-1.52)} * 100 \qquad (IX)$$

The amount by weight (in wt. %) of polymer-bonded carbonate (LC') in the reaction mixture was calculated according to formula (X):

$$LC' = \frac{[F(5.1-4.8) - F(4.5)] * 102}{N} * 100\% \qquad (X)$$

wherein the value for N ("denominator" N) is calculated according to formula (XI):

$$N=[F(5.1-4.8)-F(4.5)]*102+F(4.5)*102+F(2.4)*58+0.33*F(1.2-1.0)*58+0.25*F(1.6-1.52)*146 \qquad (XI)$$

The factor 102 results from the sum of the molar masses of $CO_2$ (molar mass 44 g/mol) and of propylene oxide (molar mass 58 g/mol), the factor 58 results from the molar mass of propylene oxide, and the factor 146 results from the molar mass of the starter used, 1,8-octanediol.

The amount by weight (in wt. %) of cyclic carbonate (CC') in the reaction mixture was calculated according to formula (XII):

$$CC' = \frac{F(4.5) * 102}{N} * 100\% \qquad (XII)$$

wherein the value for N is calculated according to formula (XI).

In order to calculate from the values of the composition of the reaction mixture the composition based on the polymer component (consisting of polyether polyol, which was synthesised from starter and propylene oxide during the activation steps carried out under $CO_2$-free conditions, and polyether carbonate polyol, synthesised from starter, propylene oxide and carbon dioxide during the activation steps carried out in the presence of $CO_2$ and during the copolymerisation), the non-polymer constituents of the reaction mixture (i.e. cyclic propylene carbonate as well as any unreacted propylene oxide present) were eliminated by calculation. The amount by weight of the carbonate repeating units in the polyether carbonate polyol was converted to an amount by weight of carbon dioxide by means of the factor $F=44/(44+58)$. The indication of the $CO_2$ content in the polyether carbonate polyol ("incorporated $CO_2$"; see following examples and Table 1) is normalised to the proportion of the polyether carbonate polyol molecule that was formed in the copolymerisation and optionally the activation steps in the presence of $CO_2$ (i.e. the proportion of the polyether carbonate polyol molecule, which results from the starter (1,8-octanediol) and from the reaction of the starter with epoxide, that was added under $CO_2$-free conditions was not taken into account here).

H-functional starter compound used:
1,8-octanediol Sigma Aldrich

Examples 1 to 7

The Catalysts were Prepared as Follows

Example 1 (Comparison)

Preparation of a DMC Catalyst without Addition of NaOH

The catalyst was prepared using an apparatus according to FIG. 4 of WO-A 01/39883.

A solution of 258 g of zinc chloride in 937 g of distilled water and 135 g of tert-butanol was circulated at 50° C. in a loop reactor containing a jet disperser according to FIG. 2 of WO-A 01/39883 with a bore (diameter 0.7 mm). A solution of 26 g of potassium hexacyanocobaltate (0.078 mol) in 332 g of distilled water was added thereto. The pressure loss in the jet disperser was 2.5 bar. The dispersion that formed was then circulated for 60 minutes at 50° C. and a pressure loss in the jet disperser of 2.5 bar. Thereafter, a mixture of 5.7 g of tert-butanol, 159 g of distilled water and 27.6 g of polypropylene glycol 1000 was added and the dispersion was then circulated for 80 minutes at 50° C. and a pressure loss in the jet disperser of 2.5 bar.

230 g of the resulting dispersion were filtered in a suction filter with a filter surface of 20 cm³ and then washed with a mixture of 82 g of tert-butanol, 42.3 g of distilled water and 1.7 g of polypropylene glycol 1000. The washed filter cake was squeezed mechanically between two strips of filter paper and finally dried for 2 hours at 60° C. under a high vacuum at about 0.05 bar (absolute).

Example 2 (Comparison)

Preparation of a DMC Catalyst with 0.25 Mol Base Equivalents Per Mol of Potassium Hexacyanocobaltate The catalyst was prepared using an apparatus according to FIG. 4 of WO-A 01/39883.

A solution of 258 g of zinc chloride in 937 g of distilled water, 135 g of tert-butanol and 7.8 g of 10% aqueous NaOH (0.0195 mol base equivalents) was circulated at 50° C. in a loop reactor containing a jet disperser according to FIG. 2 of WO-A 01/39883 with a bore (diameter 0.7 mm). A solution of 26 g of potassium hexacyanocobaltate (0.078 mol) in 332 g of distilled water was added thereto. The pressure loss in the jet disperser was 2.5 bar. The dispersion that formed was then circulated for 60 minutes at 50° C. and a pressure loss in the jet disperser of 2.5 bar. Thereafter, a mixture of 5.7 g of tert-butanol, 159 g of distilled water and 27.6 g of polypropylene glycol 1000 was added and the dispersion was then circulated for 80 minutes at 50° C. and a pressure loss in the jet disperser of 2.5 bar.

230 g of the resulting dispersion were filtered in a suction filter with a filter surface of 20 cm³ and then washed with a mixture of 82 g of tert-butanol, 42.3 g of distilled water and 1.7 g of polypropylene glycol 1000. The washed filter cake was squeezed mechanically between two strips of filter paper and finally dried for 2 hours at 60° C. under a high vacuum at about 0.05 bar (absolute).

Example 3

Preparation of a DMC Catalyst with 0.55 Mol Base Equivalents Per Mol of Potassium Hexacyanocobaltate A solution of 7.4 g (0.022 mol) of potassium hexacyanocobaltate, 39 g of tert-butanol and 302 g of distilled water was placed in a 1-liter round-bottomed flask and heated to 30° C. with vigorous stirring by means of a laboratory stirrer (1000 rpm). In the course of 3 minutes, 152 g of a 50% aqueous solution of zinc chloride (alkalinity 0.64 wt. % ZnO, corresponds to 0.012 mol base equivalents) were added dropwise to the stirred solution. Stirring was then carried out for a further 30 minutes at 30° C. (1000 rpm). The suspension that formed was filtered by means of a suction filter. 8.0 g of the moist filter cake were then dispersed, with vigorous stirring (1000 rpm), in a mixture of 110 g of tert-butanol and 60 g of distilled water. When all the solid was dispersed homogeneously in the wash solution, stirring was carried out for a further 30 minutes. The suspension was filtered again by means of a suction filter, and the moist filter cake was finally dispersed again in 144 g of tert-butanol. After filtration of the dispersion, the filter cake was dried overnight at 45° C. in vacuo (300 mbar).

Example 4

Preparation of a DMC Catalyst with 0.372 Mol Base Equivalents Per Mol of Potassium Hexacyanocobaltate The catalyst was prepared using an apparatus according to FIG. 4 of WO-A 01/39883.

A solution of 258 g of zinc chloride in 937 g of distilled water, 135 g of tert-butanol and 15.3 g of a 10% aqueous sodium carbonate solution (0.0145 mol) was circulated at 50° C. in a loop reactor containing a jet disperser according to FIG. 2 of WO-A 01/39883 with a bore (diameter 0.7 mm). A solution of 26 g of potassium hexacyanocobaltate (0.078 mol) in 332 g of distilled water was added thereto. The pressure loss in the jet disperser was 2.5 bar. The dispersion that formed was then circulated for 60 minutes at 50° C. and a pressure loss in the jet disperser of 2.5 bar. Thereafter, a mixture of 5.7 g of tert-butanol, 159 g of distilled water and 27.6 g of polypropylene glycol 1000 was added and the dispersion was then circulated for 80 minutes at 50° C. and a pressure loss in the jet disperser of 2.5 bar.

230 g of the resulting dispersion were filtered in a suction filter with a filter surface of 20 cm³ and then washed with a mixture of 82 g of tert-butanol, 42.3 g of distilled water and 1.7 g of polypropylene glycol 1000. The washed filter cake was squeezed mechanically between two strips of filter paper and finally dried for 2 hours at 60° C. under a high vacuum at about 0.05 bar (absolute).

Example 5 (Comparison)

Preparation of a DMC Catalyst with 0.20 Mol Base Equivalents Per Mol of Potassium Hexacyanocobaltate The catalyst was prepared using an apparatus according to FIG. 4 of WO-A 01/39883.

A solution of 258 g of zinc chloride in 937 g of distilled water, 135 g of tert-butanol and 15.3 g of a 10% aqueous sodium monomethyl carbonate solution (0.0156 mol) was circulated at 50° C. in a loop reactor containing a jet disperser according to FIG. 2 of WO-A 01/39883 with a bore (diameter 0.7 mm). A solution of 26 g of potassium hexacyanocobaltate (0.078 mol) in 332 g of distilled water was added thereto. The pressure loss in the jet disperser was 2.5 bar. The dispersion that formed was then circulated for 60 minutes at 50° C. and a pressure loss in the jet disperser of 2.5 bar. Thereafter, a mixture of 5.7 g of tert-butanol, 159 g of distilled water and 27.6 g of polypropylene glycol 1000 was added and the dispersion was then circulated for 80 minutes at 50° C. and a pressure loss in the jet disperser of 2.5 bar.

230 g of the resulting dispersion were filtered in a suction filter with a filter surface of 20 cm$^3$ and then washed with a mixture of 82 g of tert-butanol, 42.3 g of distilled water and 1.7 g of polypropylene glycol 1000. The washed filter cake was squeezed mechanically between two strips of filter paper and finally dried for 2 hours at 60° C. under a high vacuum at about 0.05 bar (absolute).

Example 6

Preparation of a DMC Catalyst with 1.25 Mol Base Equivalents Per Mol of Potassium Hexacyanocobaltate The catalyst was prepared using an apparatus according to FIG. 4 of WO-A 01/39883.

A solution of 427 g of zinc bromide in 937 g of distilled water, 135 g of tert-butanol and 39.0 g of 10% aqueous NaOH (0.0975 mol) was circulated at 50° C. in a loop reactor containing a jet disperser according to FIG. 2 of WO-A 01/39883 with a bore (diameter 0.7 mm). A solution of 26 g of potassium hexacyanocobaltate (0.078 mol) in 332 g of distilled water was added thereto. The pressure loss in the jet disperser was 2.5 bar. The dispersion that formed was then circulated for 60 minutes at 50° C. and a pressure loss in the jet disperser of 2.5 bar. Thereafter, a mixture of 5.7 g of tert-butanol, 159 g of distilled water and 27.6 g of polypropylene glycol 1000 was added and the dispersion was then circulated for 80 minutes at 50° C. and a pressure loss in the jet disperser of 2.5 bar.

230 g of the resulting dispersion were filtered in a suction filter with a filter surface of 20 cm$^3$ and then washed with a mixture of 82 g of tert-butanol, 42.3 g of distilled water and 1.7 g of polypropylene glycol 1000. The washed filter cake was squeezed mechanically between two strips of filter paper and finally dried for 2 hours at 60° C. under a high vacuum at about 0.05 bar (absolute).

Example 7 (Comparison)

Preparation of a DMC Catalyst with 2.0 Mol Base Equivalents Per Mol of Potassium Hexacyanocobaltate The catalyst was prepared using an apparatus according to FIG. 4 of WO-A 01/39883.

A solution of 427 g of zinc bromide in 937 g of distilled water, 135 g of tert-butanol and 62.4 g of 10% aqueous NaOH (0.156 mol) was circulated at 50° C. in a loop reactor containing a jet disperser according to FIG. 2 of WO-A 01/39883 with a bore (diameter 0.7 mm). A solution of 26 g of potassium hexacyanocobaltate (0.078 mol) in 332 g of distilled water was added thereto. The pressure loss in the jet disperser was 2.5 bar. The dispersion that formed was then circulated for 60 minutes at 50° C. and a pressure loss in the jet disperser of 2.5 bar. Thereafter, a mixture of 5.7 g of tert-butanol, 159 g of distilled water and 27.6 g of polypropylene glycol 1000 was added and the dispersion was then circulated for 80 minutes at 50° C. and a pressure loss in the jet disperser of 2.5 bar.

230 g of the resulting dispersion were filtered in a suction filter with a filter surface of 20 cm$^3$ and then washed with a mixture of 82 g of tert-butanol, 42.3 g of distilled water and 1.7 g of polypropylene glycol 1000. The washed filter cake was squeezed mechanically between two strips of filter paper and finally dried for 2 hours at 60° C. under a high vacuum at about 0.05 bar (absolute).

Examples 8 to 14

The Catalysts were Tested as Follows in the Preparation of Polyether Carbonate Polyols 141 mg of dried DMC catalyst according to one of Examples 1 to 7 (see Table 1 below) and 51 g of dried 1,8-octanediol (starter) were placed in a 1-liter pressurised reactor with a gas-metering device. The reactor was heated to 130° C. and rendered inert by repeated application of nitrogen to about 5 bar and subsequent pressure reduction to about 1 bar. This procedure was carried out 3 times. 25 g of propylene oxide (PO) were quickly metered into the reactor at 130° C. and in the absence of $CO_2$. Activation of the catalyst was marked by a temperature peak ("hotspot") and by a pressure drop to the starting pressure (about 1 bar). After the first pressure drop, 20 g of PO and then 19 g of PO were quickly metered in, as a result of which a temperature peak and a pressure drop again occurred in each case. After 50 bar $CO_2$ had been applied to the reactor, 50 g of PO were quickly metered in, a temperature peak occurring after a waiting time [time 1]. At the same time, the carbon dioxide $CO_2$ pressure started to fall. The pressure was so regulated that fresh $CO_2$ was added when the pressure fell below a desired value. Only then was the remaining propylene oxide (435 g) pumped continuously into the reactor at about 1.8 g/minute, while after 10 minutes the temperature was lowered to 105° C. in steps of 5° C. per five minutes. When the PO addition was complete, stirring (1500 rpm) was continued at 105° C. and the pressure indicated above until no further $CO_2$ consumption was observed.

TABLE 1

Preparation of polyether carbonate polyols

| Example | Catalyst used from Example | Alkalinity [mol base equiv. per mol of $K_3[Co(CN)_6]$] | Time 1 [min] | Incorporated $CO_2$ [wt. %] | Selectivity cyclic/linear | OH number [mg/g] | Poly-dispersity |
|---|---|---|---|---|---|---|---|
| 8 (comp.) | 1 (comp.) | — | 30 | 21.0 | 0.20 | 65.5 | 1.70 |
| 9 (comp.) | 2 (comp.) | 0.25 | 38 | 21.0 | 0.21 | 64.6 | 1.52 |

TABLE 1-continued

Preparation of polyether carbonate polyols

| Example | Catalyst used from Example | Alkalinity [mol base equiv. per mol of $K_3[Co(CN)_6]$] | Time 1 [min] | Incorporated $CO_2$ [wt. %] | Selectivity cyclic/linear | OH number [mg/g] | Poly-dispersity |
|---|---|---|---|---|---|---|---|
| 10 | 3 | 0.55 | 74 | 19.3 | 0.16 | 66.6 | 1.68 |
| 11 | 4 | 0.372 | 58 | 18.7 | 0.17 | 65.3 | 1.52 |
| 12 (comp.) | 5 (comp.) | 0.20 | 114 | 22.4 | 0.22 | 75.2 | 1.91 |
| 13 | 6 | 1.25 | 50 | 18.8 | 0.14 | 48.7 * | 1.44 |
| 14 (comp.) | 7 (comp.) | 2.0 | 188 | 18.5 | 0.14 | 57.3 * | 1.59 | comp. = comparison example
* OH number of the reaction mixture, propylene carbonate formed not being separated off beforehand It is clear from the results of Table 1 that a minimum amount of base is necessary to achieve an improvement in the selectivity relative to a DMC catalyst without added base. For example, the selectivity without added base (Ex. 8 (comp.)) is not improved by addition of 0.2 (Ex. 12 (comp.) or 0.25 (Ex. 9 (comp.)) base equivalents per mol of $K_3[Co(CN)_6]$ in the preparation of the DMC catalyst. Only from an alkalinity of more than 0.25 base equivalents per mol of $K_3[Co(CN)_6]$, for example 0.37 base equivalents per mol of $K_3[Co(CN)_6]$ according to Ex. 11, is the selectivity improved in favour of the desired linear polyether carbonate polyol. Too high an amount of base equivalents per mol of $K_3[Co(CN)_6]$, on the other hand, impairs the economy of the process; even an amount of only 2.0 mol base equivalents per mol of $K_3[Co(CN)_6]$ lengthens time 1 to more than 120 minutes (Ex. 14 (comp.)).

The invention claimed is:

1. A process for preparing a polyether carbonate polyol consisting of reacting one or more H-functional starter substances, one or more alkylene oxides, and carbon dioxide in the presence of at least one double metal cyanide catalyst prepared from a cyanide-free metal salt and a potassium hexacyanocobaltate(III) salt, wherein said cyanide-free metal salt and/or said potassium hexacyanocobaltate(III) salt comprises from 0.3 to 1.8 mol base equivalents, based on 1 mol of said metal cyanide salt, of an alkaline metal hydroxide, metal carbonate, and/or metal oxide, wherein said at least one double metal cyanide catalyst is prepared by reacting an aqueous solution of said cyanide-free metal salt with an aqueous solution of said potassium hexacyanocobaltate(III) salt in the presence of one or more organic complex ligands, wherein said aqueous solution of said cyanide-free metal salt and/or said aqueous solution of said potassium hexacyanocobaltate (III) salt comprises one or more alkaline metal hydroxides, metal carbonates, and/or metal oxides, and wherein the total amount of said one or more alkaline metal hydroxides, metal carbonates, and/or metal oxides used is in the range of from 0.3 to 1.8 mol base equivalents, based on 1 mol of the potassium hexacyanocobaltate(III) salt.

2. The process of claim 1, wherein said at least one double metal cyanide catalyst is prepared by
(i) reacting an aqueous solution of said cyanide-free metal salt with an aqueous solution of said potassium hexacyanocobaltate(III) salt in the presence of one or more organic complex ligands, wherein said aqueous solution of said cyanide-free metal salt and/or aqueous solution of said potassium hexacyanocobaltate(III) salt comprises one or more alkaline metal hydroxides and/or metal carbonates and/or metal oxides, and wherein the total amount of said one or more alkaline metal hydroxides and/or metal carbonates and/or metal oxides used is in the range of from 0.3 to 1.8 mol base equivalents, based on 1 mol of the potassium hexacyanocobaltate (III) salt, to obtain a suspension;
(ii) separating the solid from the suspension obtained in step (i);
(iii) washing the solid of step (ii) with an aqueous solution of an organic complex ligand;
(iv) drying the solid of step (iii);
wherein one or more organic complex ligands are added in step (i) or immediately after step (ii).

3. The process of claim 1, wherein said cyanide-free metal salt and/or said potassium hexacyanocobaltate(III) salt comprise from 0.6 to 1.6 mol base equivalents, based on 1 mol of the potassium hexacyanocobaltate(III) salt, of an alkaline metal hydroxide, metal carbonate, and/or metal oxide.

4. The process of claim 1, wherein said alkaline metal hydroxide, metal carbonate, and/or metal oxide is selected from the group consisting of the oxides of metals of groups 1a and 2a of the periodic table of the elements, hydroxides of metals of groups 1a and 2a of the periodic table of the elements, and mixtures thereof.

5. The process of claim 4, wherein said alkaline metal hydroxide, metal oxide, and/or metal carbonate is selected from the group consisting of sodium carbonate, sodium hydroxide, potassium hydroxide, potassium carbonate, calcium oxide, calcium hydroxide, barium hydroxide, barium oxide, and mixtures thereof.

6. The process of claim 1, wherein said cyanide-free metal salt is selected from the group consisting of zinc chloride, zinc bromide, zinc iodide, zinc acetate, zinc acetylacetonate, zinc benzoate, zinc nitrate, iron(II) sulfate, iron(II) bromide, iron(II) chloride, cobalt(II) chloride, cobalt(II) thiocyanate, nickel(II) chloride, nickel(II) nitrate, and mixtures thereof.

7. The process of claim 1, wherein
(a) said one or more H-functional starter substances and said at least one double metal cyanide catalyst is placed in a reaction vessel and optionally dried by the removal of water and/or other readily volatile compounds via elevated temperature and/or reduced pressure to obtain a mixture, wherein said at least one double metal cyanide catalyst is added to said H-functional starter substance before or after drying;
(b1) in a first activation step, adding a first partial amount, based on the total amount of alkylene oxides used in the activation and copolymerisation, of one or more alkylene oxides to the mixture obtained in step (a) and observing a waiting period until a temperature peak occurs as a result of the subsequent exothermic chemical reaction and/or a pressure drop in the reactor to obtain a mixture;

(b2) in a second activation step, after the temperature peak reached in step (b1), adding a second partial amount, based on the total amount of alkylene oxides used in the activation and copolymerisation, of one or more alkylene oxides to the mixture obtained in step (b1) and observing a waiting period until a temperature peak occurs as a result of the subsequent exothermic chemical reaction and/or a pressure drop in the reactor to obtain a mixture; and (c) adding one or more alkylene oxides and carbon dioxide to the mixture obtained in step (b2).

8. The process of claim 7, wherein the reaction of said alkylene oxides and carbon dioxide takes place under a pressure of from 1 to 200 bar.

9. The process of claim 7, wherein the reaction of said alkylene oxides and carbon dioxide takes place at a temperature in the range of from 60 to 150° C.

10. The process of claim 7, wherein said process is carried out in a tubular reactor, stirrer vessel, or loop reactor.

11. The process of claim 7, wherein said process is carried out in a stirrer vessel and wherein in step c) one or more H-functional starter compounds are metered continuously into the reactor during the reaction.

* * * * *